US009474632B2

(12) United States Patent
Bosscher et al.

(10) Patent No.: US 9,474,632 B2
(45) Date of Patent: Oct. 25, 2016

(54) ROBOTIC EXOSKELETON WITH FALL CONTROL AND ACTUATION

(71) Applicant: HARRIS CORPORATION, Melbourne, FL (US)

(72) Inventors: Paul M. Bosscher, West Melbourne, FL (US); Matthew D. Summer, Melbourne, FL (US); Loran J. Wilkinson, Palm Bay, FL (US)

(73) Assignee: Harris Corporation, Melbourne, FL (US)

( * ) Notice: Subject to any disclaimer, the term of this patent is extended or adjusted under 35 U.S.C. 154(b) by 0 days.

(21) Appl. No.: 14/458,766

(22) Filed: Aug. 13, 2014

(65) Prior Publication Data

US 2015/0289997 A1    Oct. 15, 2015

Related U.S. Application Data

(60) Provisional application No. 61/978,545, filed on Apr. 11, 2014.

(51) Int. Cl.
| | |
|---|---|
| *G05B 19/04* | (2006.01) |
| *A61F 2/60* | (2006.01) |
| *B25J 19/00* | (2006.01) |
| *B25J 9/00* | (2006.01) |
| *A61F 2/68* | (2006.01) |
| *A61F 2/70* | (2006.01) |

(Continued)

(52) U.S. Cl.
CPC . *A61F 2/60* (2013.01); *A61F 2/68* (2013.01); *A61F 2/70* (2013.01); *B25J 9/0006* (2013.01); *B25J 19/0091* (2013.01); *A61F 2002/5081* (2013.01); *A61F 2002/701* (2013.01); *A61F 2002/741* (2013.01); *A61F 2002/745* (2013.01); *Y10S 901/49* (2013.01)

(58) Field of Classification Search
USPC ............ 700/245, 258, 261, 246, 250; 602/6; 600/587, 592, 595; 901/27, 28, 46; 318/8, 9, 17
See application file for complete search history.

(56) References Cited

U.S. PATENT DOCUMENTS

| 5,516,249 A | 5/1996 | Brimhall |
|---|---|---|
| 5,583,478 A | 12/1996 | Renzi |

(Continued)

OTHER PUBLICATIONS

Rahman, T., et al., "Passive Exoskeletons for Assisting Limb Movement," Journal of Rehabilitation Research & Development, vol. 43, No. 5, pp. 583-590, Aug./Sep. 2006, DOI: 10.1682/JRRD.2005.04.0070.

(Continued)

*Primary Examiner* — Ronnie Mancho
(74) *Attorney, Agent, or Firm* — Fox Rothschild LLP; Robert J. Sacco; Carol E. Thorstad-Forsyth

(57) ABSTRACT

Method for controlling an exoskeleton (100) involves detecting an occurrence of an uncontrolled acceleration of at least a portion of the exoskeleton, as might occur during a fall. In response, the exoskeleton is caused to automatically transition at least one motion actuator (104*a*, 104*b*) from a first operational state to a second operational state. In the first operational state, the one or more motion actuators are configured to provide a motive force for controlled movement of the exoskeleton. In the second operational state, the one or more motion actuators are configured to function as energy dampers which dissipate a shock load exerted upon the exoskeleton.

21 Claims, 4 Drawing Sheets

(51) Int. Cl.
A61F 2/50 (2006.01)
A61F 2/74 (2006.01)

(56) References Cited

U.S. PATENT DOCUMENTS

| | | | |
|---|---|---|---|
| 7,190,141 | B1 | 3/2007 | Ashrafiuon et al. |
| 7,300,824 | B2 | 11/2007 | Sheats |
| 7,665,641 | B2 | 2/2010 | Kaufman |
| 7,774,177 | B2 | 8/2010 | Dariush |
| 7,947,004 | B2 | 5/2011 | Kazerooni et al. |
| 8,142,370 | B2 | 3/2012 | Weinberg et al. |
| 8,419,804 | B2 | 4/2013 | Herr et al. |
| 8,702,811 | B2 | 4/2014 | Ragnarsdottir et al. |
| 8,849,457 | B2 | 9/2014 | Jacobsen et al. |
| 8,986,397 | B2 | 3/2015 | Bedard et al. |
| 9,066,817 | B2 | 6/2015 | Gilbert et al. |
| 2006/0079817 | A1 | 4/2006 | Dewald et al. |
| 2007/0123997 | A1 | 5/2007 | Herr et al. |
| 2008/0009771 | A1* | 1/2008 | Perry .............. B25J 9/0006 600/587 |
| 2008/0249438 | A1 | 10/2008 | Agrawal et al. |
| 2009/0255531 | A1 | 10/2009 | Johnson et al. |
| 2010/0113980 | A1* | 5/2010 | Herr .............. A61F 2/60 600/587 |
| 2010/0114329 | A1* | 5/2010 | Casler .............. B25J 19/0008 623/24 |
| 2011/0040216 | A1 | 2/2011 | Herr et al. |
| 2011/0266323 | A1 | 11/2011 | Kazerooni et al. |
| 2012/0156661 | A1 | 6/2012 | Smith et al. |
| 2012/0259431 | A1 | 10/2012 | Han et al. |
| 2013/0102935 | A1 | 4/2013 | Kazerooni et al. |
| 2013/0296746 | A1 | 11/2013 | Herr et al. |
| 2013/0310979 | A1 | 11/2013 | Herr et al. |
| 2014/0094728 | A1 | 4/2014 | Soderberg et al. |
| 2015/0088043 | A1 | 3/2015 | Goldfield et al. |
| 2015/0289995 | A1 | 10/2015 | Wilkinson et al. |

OTHER PUBLICATIONS

Rosen, J., et al., "A Myosignal-Based Powered Exoskeleton System," IEE Transaction on Systems, Man, and Cybernetics—Part A: Systems and Humans, vol. 31, No. 3, May 2001, 1083-4427/01, copyright 2001 IEEE.

Burkard, H., et al., "An Ultra-Thin, Highly Flexible Multilayer," http://www.hightec.ch/uploads.media/An_ultra-thin_highly_flexible_multilayer_2007_01.pdf.

Banala, S.K., et al., "Gravity-Balancing Leg Orthosis and Its Performance Evaluation," IEEE Transactions on Robotics, vol. 22, No. 6, Dec. 2006, 1552-3098, copyright 20006 IEEE.

Goswami, A., "Active Empedance: A Noval Concept in Assistive Exoskeleton Control," Exoskeleton Control Using Active Impedance, This work is a collaboration with Prof. Ed Colgate, Prof. Michael Peshkin and Gbriel-Aguirre Ollinger of Northwestern University, Evanston, Illinois, page last updated Sep. 24, 2012.

Huang, J., et al., "Human Motion Assistance Using Waling-Aid Robot and Wearable Sensors," In Proceedings of the International Congress on Neurotechnology, Electronics and Informatics (RoboAssist-2013), pp. 199-204, ISBN: 978-989-8565-80-8, DOI: 10.5220/0004664101990204, copyright 2013 SCITEPRESS (Science and Technology Publications, Lda.).

Wolbrecht, E.T., et al., "Pneumatic Control of Robots for Rehabilitation," The International Journal of Robotics Research, vol. 29, No. 1, Jan. 2010, pp. 23-38, DOI: 10.1177/0278364909103787, copyright The Author(s), 2010.

Debicki, D.B., et al., "Inter-Joint Coupling Strategy During Adaptation to Novel Viscous Loads in Human Arm Movement," J. Neurophysiol 92: 754-765, 2004, 10.1152/jn.00119.2004, 022-3077/04, copyright 2004 The American Physiological Society.

Jung, J., et al., "Walking Intent Detection Algorithy for Paraplegic Patients Using a Robotic Exoskeleton Waling Assistant with Crutches," International Journal of Control, Automatiion, and Systems (2012) 10(5):954-962 DOI: 10.1007/s12555-01200512-4, ISSN:1598-6446 eISSN:2005-4092; copyright ICROS, KIEE and Springer 2012.

Lenzi, T., et al , "Intention-Based EMG Control for Powered Exoskeletons," IEEE Transactions of Biomedical Engineering, vol. 59, No. 8, Aug. 2012, 0018-9294 copyright 2012 IEEE.

Dorrier, Jason, "New Upper Body Bionic Suit Uses Air to Lift Loads of 50 Kilograms," Oct. 16, 2012, Augmentation, Video Post, http://singularityhub.com/2012/10/16/new-upper-body-bionic-suit-uses-air-to-lift-loads-of-50-kilograms/.

Black, Thomas, Business Bet on Iron Man-Like Exoskeletons, Businessweek, Mar. 28, 2013 http://www.bloomberg.com/bw/articles/2013-03-28/businesses-bet-on-iron-man-like-exoskeletons.

Upbin, Bruce, "This Amazing Robot Exoskeleton Helps the Paralyzed Walk Again," Nov. 8, 2013, Forbes.

Bowdler, Neil, "Rise of the Human Exoskeletons," Technology, BBC News, Mar. 4, 2014.

Robotics Laboratory, "Static and Dynamic Balancing of Parallel Mechanisms," University Laval, copyright 1997-2015 Laboratoire de robotique.

Robotics (http://news.discovery.com/tech/robotics), "I am Iron Man: Top 5 Exoskeleton Robots," Nov. 27, 2012, Associated Press,U.S. Army.

Huang, J., et al., "Human Motion Assistance Using Walking-Aid Robot and Wearable Sensors," Abstract Only, RoboAssist 2013—Special Session on Wearable Robotics for Motion Assistance and Rehabilitation Abstracts, http://neurotechnix/org/Abstracts/2013/RoboAssist)2013_Abstracts/htm.

* cited by examiner

ROBOTIC EXOSKELETON WITH FALL CONTROL AND ACTUATION

CROSS REFERENCE TO RELATED APPLICATIONS

This application claims the benefit of U.S. Provisional Patent Application No. 61/978,545, filed Apr. 11, 2014, the entirety of which is incorporated herein by reference.

BACKGROUND OF THE INVENTION

1. Statement of Technical Field

The inventive arrangements relate to robotic exoskeletons and more particularly to robotic exoskeletons having advanced control systems that facilitate user safety.

2. Description of the Related Art

A robotic exoskeleton is a machine that is worn by a human user. Such machines typically comprise a structural frame formed of a plurality of rigid structural members. The structural members are usually connected to each other at a plurality of locations where joints or articulated members allow movement of the structural members in a manner that corresponds to movement in accordance with the human anatomy. When the exoskeleton is worn by a user, the location of the robotic joints will usually correspond to the location of joints in the human anatomy. Motive elements, which are sometimes called actuators, are commonly used to facilitate movement of the rigid structural members that comprise the exoskeleton. These motive elements or actuators commonly include hydraulic actuators, pneumatic actuators and/or electric motors. Various exoskeleton designs for humans have been proposed for the full body, lower body only, and upper body only.

An exoskeleton includes a power source power to operate the motive elements or actuators. The power source for such devices can be an on-board system (e.g. batteries, or fuel driven power generator carried on the exoskeleton). Alternatively, some exoskeleton designs have a wire or cable tether which supplies power (e.g. electric or hydraulic power) from a source which is otherwise physically independent of the exoskeleton. An on-board control system is provided in many exoskeletons to allow a user to control certain operations of the exoskeleton. Due to the close interaction of the exoskeleton with the human operator, such a control system for the exoskeleton must be carefully designed to facilitate ease of use and operator safety.

Robotic exoskeletons as described herein can provide users with advantages of increased strength, endurance and mobility. The motive elements used to produce movement of the structural members forming the exoskeleton can in many designs exert forces that far exceed the strength and/or endurance of a human. Exoskeletons can also potentially increase user safety and help control certain desired motions. As such, robotic exoskeletons are of increasing interest for use in a wide variety of applications. For example, robotic exoskeletons have potential for use in the fields of healthcare, physical rehabilitation, and public service (police, first responders). They also show promise for use in areas such as human augmentation.

SUMMARY OF THE INVENTION

The invention concerns a method for preventing injury to a user of a robotic exoskeleton. The method involves detecting an occurrence of an uncontrolled acceleration of at least a portion of the exoskeleton, as might occur during a fall. In response to detecting such uncontrolled acceleration, the exoskeleton is caused to automatically transition at least one motion actuator from a first operational state to a second operational state. In the first operational state, the one or more motion actuators are configured to provide a motive force for controlled movement of the exoskeleton. In the second operational state, the one or more motion actuators are configured to function as energy dampers which dissipate a shock load exerted upon the exoskeleton.

According to another aspect, the invention concerns an exoskeleton system that is configured to be worn by a human operator. The exoskeleton system includes a control system and a plurality of motion actuators responsive to the control system. The motion actuators and control system function cooperatively to facilitate movement of structural members comprising the exoskeleton. Sensors are provided as part of the exoskeleton to sense movement of a various human body parts associated with the operator. The data from these sensors is communicated to the exoskeleton control system as sensor data concerning such movements. The exoskeleton control system utilizes the sensor data to selectively actuate the plurality of motion actuators, thereby causing movement of the exoskeleton. This movement of the exoskeleton will generally correspond to the movement of the human body parts which has been sensed. Notably, the motion actuators are arranged to selectively transition from a first operational state to a second operational state in response to signals from the control system. In the first operational state, the motion actuators are configured to provide a motive force for controlled movement of the exoskeleton structure. In the second operational state the motion actuators are configured to function as a damper to dissipate a shock load exerted upon the exoskeleton.

BRIEF DESCRIPTION OF THE DRAWINGS

Embodiments will be described with reference to the following drawing figures, in which like numerals represent like items throughout the figures, and in which.

DETAILED DESCRIPTION

Figure 1:
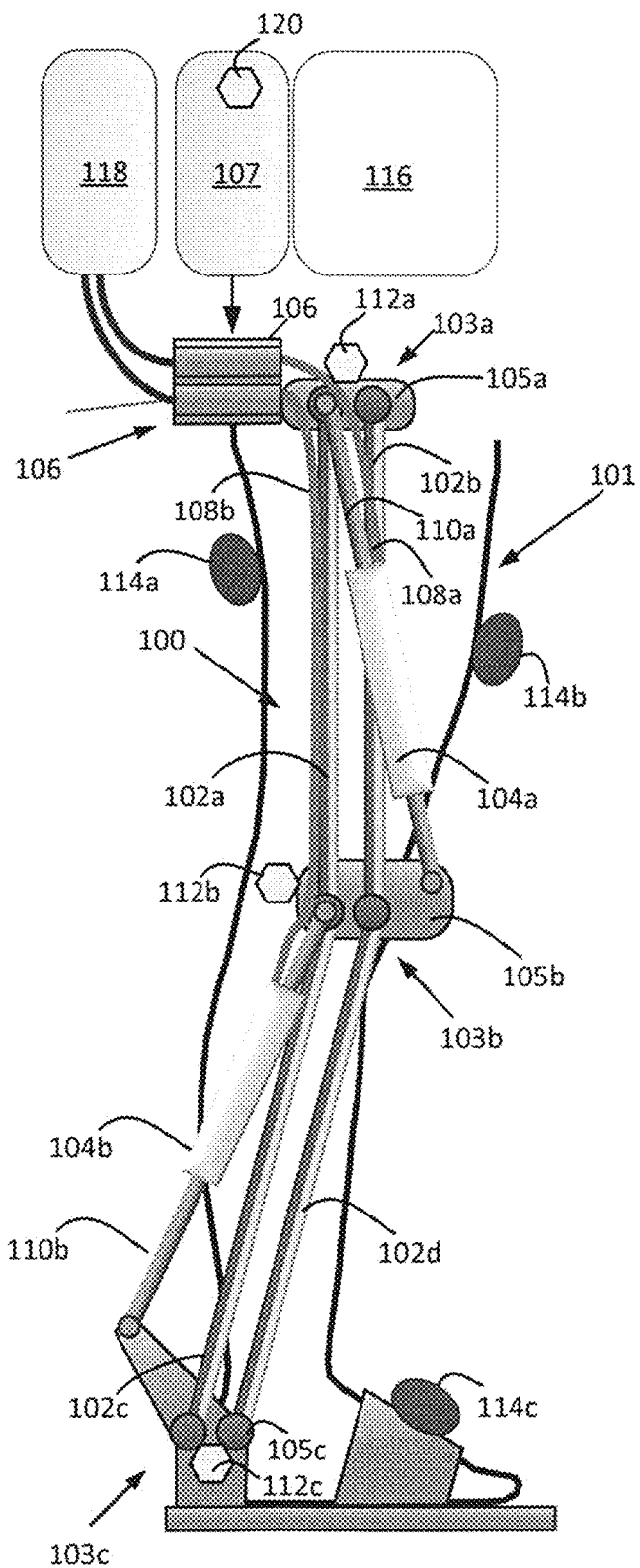
FIG. 1 is a drawing that is useful for understanding the various elements of an exoskeleton that provides improved operator safety.

The invention is described with reference to the attached figures. The figures are not drawn to scale and they are provided merely to illustrate the instant invention. Several aspects of the invention are described below with reference to example applications for illustration. It should be understood that numerous specific details, relationships, and methods are set forth to provide a full understanding of the invention. One having ordinary skill in the relevant art, however, will readily recognize that the invention can be practiced without one or more of the specific details or with other methods. In other instances, well-known structures or operation are not shown in detail to avoid obscuring the invention. The invention is not limited by the illustrated ordering of acts or events, as some acts may occur in different orders and/or concurrently with other acts or events. Furthermore, not all illustrated acts or events are required to implement a methodology in accordance with the invention.

Robotic exoskeletons commonly include structural members which are movably operated by means of one or more actuators. While offering many benefits, these structural members are often very stiff and/or rigid and therefor do not effectively absorb or dissipate energy. Under certain conditions, this stiffness can cause an injury to a user. For example, when a user who is wearing an exoskeleton encounters a sudden fall or drop, it will naturally result in a rapid and uncontrolled downward movement of the exoskeleton and person wearing same. Situations where this can occur can be intentional (jumping off of a ladder or ledge) or unintentional (tripping). In either scenario, the uncontrolled downward movement from a higher to a lower level will usually involve an initial downward acceleration and a forceful impact at the lower level involving rapid deceleration. Since a conventional exoskeleton is quite rigid under normal operating conditions, it will tend to communicate impact forces to the user wearing such exoskeleton. The foregoing problem can be solved by adding energy absorbing material (e.g. soft padding) between the operator and the exoskeleton. However, the addition of such padding is not optimal because it will increase bulk and tend to degrade performance.

Accordingly, a robotic exoskeleton in accordance with the inventive arrangements can detect an occurrence of an uncontrolled acceleration of at least a portion of the exoskeleton, as might occur during a fall. A control system and one or more sensors communicating with the control system can facilitate detection of the fall. In response to detecting such uncontrolled acceleration, the control system causes the exoskeleton to automatically transition one or more of its motion actuators from a first operational state to a second operational state. In the first operational state, such motion actuators are configured for normal exoskeleton operations wherein they provide a motive force for controlled movement of the exoskeleton. In the second operational state, the one or more motion actuators are configured to function as energy dampers which dissipate a shock load exerted upon the exoskeleton. After the shock load has been dissipated in this way, the motion actuators are transitioned back to the first operating state.

Referring now to FIG. 1 there is shown a portion of an exemplary exoskeleton 100 comprised of a structural framework. For convenience, the portion of the exoskeleton shown in FIG. 1 is from the waist down. However, it should be understood that the inventive arrangements described herein can also apply to other selected portions of an exoskeleton, such as an upper portion of an exoskeleton worn on an upper body part of user. The exoskeleton 100 is formed of a plurality of rigid structural members 102a, 102b, 102c, and 102d which are connected to each other at a plurality of joint locations 103a, 103b, 103c where one or more robot joints 105a, 105b, 105c are provided. The joint locations and the robot joints are arranged to facilitate movement of the rigid structural members in a manner that at least partially corresponds to movement in accordance with the human anatomy of a user when the suit is worn. For example, when a user 101 who wears the exoskeleton 100 bends his knee, the structural members 102a, 102b, 102c, and 102d will pivot at robot joint 105b to facilitate such user movement. From the foregoing, it will be appreciate that the rigid structural members and the plurality of robot joints comprising an exoskeleton can be fitted to and move with at least one part of a user 101 such as an upper body portion which extends above the waist, a lower body portion which extends below the waist, and a full body portion comprising the upper and lower body.

The exoskeleton 100 also includes one or more motion actuators 104a, 104b. One or more of the motion actuators can be comprised of pneumatic actuators such as pneumatically operated pistons as shown. Still, the invention is not limited in this regard and other types of motion actuators may also be used. For example, one or more of the motion actuators can optionally be comprised of hydraulic actuators, and/or electric motors.

In operation, the motion actuators 104a, 104b exert motive forces directly or indirectly upon the structural members 102a, 102b, 102c, and 102d to facilitate movement and other operations associated with the exoskeleton 100. For example, in the case of the pneumatic type actuators shown in FIG. 1, pressurized gas or air is communicated to an internal cylinder (not shown) associated with the actuator. The operation of pneumatic actuators is well known in the art and therefore will not be described here in detail. However, it will be appreciated that the pressurized air in the cylinder can drives a piston (not shown) that is coupled to a rod 110a, 110b. The rod is connected to the exoskeleton structure at a suitable location, such as robot joint 105a, 105c. The flow of pressurized air or gas to the cylinder of the pneumatic actuator can be communicated by any suitable means such as pneumatic air lines 108a, 108b. One or more valves 106 can control a flow of air to the pneumatic actuators. These valves can also be arranged to facilitate controlled venting of air from within the pneumatic actuators under certain conditions which are described below in greater detail.

From the foregoing it will be appreciated that the motion actuators 104a, 104b can have two operational states. In the first operational state, the one or more motion actuators 104a, 104b provide a motive force for movement of structural members 102a-102d. For example this operational state exists when high pressure air is being communicated to a pneumatic actuator cylinder to cause some type of controlled movement of an actuator rod 110a, 110b. In the second operational state the one or more motion actuators are configured to function as energy absorbing dampers which dissipate a shock load exerted upon the exoskeleton. For example, this operational state exists when a valve 106 selectively allows a flow of air to be vented from a cylinder of a pneumatic actuator.

Of course, similar results can be obtained with other types of motion actuators and the invention is not intended to be limited to pneumatic actuators. For example the motion actuators 104a, 104b can instead be implemented as electric motors or hydraulic actuators. If an electric motor is used for this purpose, the first operational state is achieved by applying a voltage source to the electric motor. The second operational state would be achieved by disconnecting the voltage source and automatically coupling a dissipating resistor to the power terminals of the electric motor. The motor/resistor circuit combination would then act as a damper. Similarly, if hydraulic actuators are used, one or more fluid valves could be used so that hydraulic fluid contained within a hydraulic actuator hoses flows through fluid baffles, thereby causing the hydraulic actuator to function as an energy damper. In each case, the amount of damping can be selectively controllable (either by changing the dissipative resistance (electric motors) or by changing the size of an orifice or valve opening (pneumatic actuators, hydraulic actuators).

A control system 107 can facilitate operator control of the exoskeleton actuators to carry out exoskeleton movements and operations. These movements and operations can include conventional exoskeleton operations and additional safety related operations as described herein. A control system 107 used with the inventive arrangements can comprise any suitable combination of hardware and software to carry out the control functions described herein. As such, the control system can comprise a computer processor programmed with a set of instructions, a programmable microcontroller or any other type of controller. The control system can be arranged to communicate with one or more controlled elements associated with the actuators for carrying out the operator safety operations described herein. For example, in the exemplary exoskeleton system 100 shown in FIG. 1, the controlled elements can include valves 106 associated with the pneumatic actuators 104a, 104b which valves are opened and closed in response to signals from the control system. Pneumatic air lines 108a, 108b can be used to pneumatically couple the pneumatic actuators to the valves. The valves can be controlled by control system 107 electronically or by any other suitable means.

The exoskeleton will include a plurality of sensors which communicate sensor data to the control system 107. For example sensors 112a, 112b, 112c can be provided at one or more robot joints to provide sensor data regarding a position, a displacement and/or an acceleration of one or more structural members 102a, 102b, 102c, 102d relative to other parts of the exoskeleton. Additional sensors 114a, 114b, 114c can be provided to sense movements or forces exerted by the user 101 upon the exoskeleton 100. Output sensor data from these additional sensors 114a, 114b, 114c can be interpreted by control system 107 as control signals which can cause certain operations of motion actuators 104a, 104b. For example, the control system can respond to inputs from such sensors to activate certain motion actuators for effecting movement of the exoskeleton. Finally, one or more sensors 120 can be provided to measure overall acceleration and or velocity of an exoskeleton 100. As such, sensor(s) 120 are somewhat different as compared to the other sensors described herein insofar as it does not measure relative movement among the various structural elements comprising the exoskeleton, but rather measures the acceleration or velocity of the exoskeleton as a whole relative to an external frame of reference (e.g. relative to the earth). Connections between the various sensors and the control system are omitted in FIG. 1 to avoid obscuring the invention. However, it will be appreciated by those skilled in the art that suitable wired or wireless connections are provided to communicate sensor data from each sensor to the control system.

A suitable power source 116 is provided for powering operations of the exoskeleton. The power source can provide a source of electrical power for electronic components, such as the control system. For exoskeletons that use pneumatic or hydraulic actuators, the exoskeleton can also include a source 118 of pressurized air or hydraulic fluid. The power source 116 and the source 118 of pressurized air can be carried on-board the exoskeleton or can be provided from a remote base unit by means of a tether arrangement.

Figure 2:
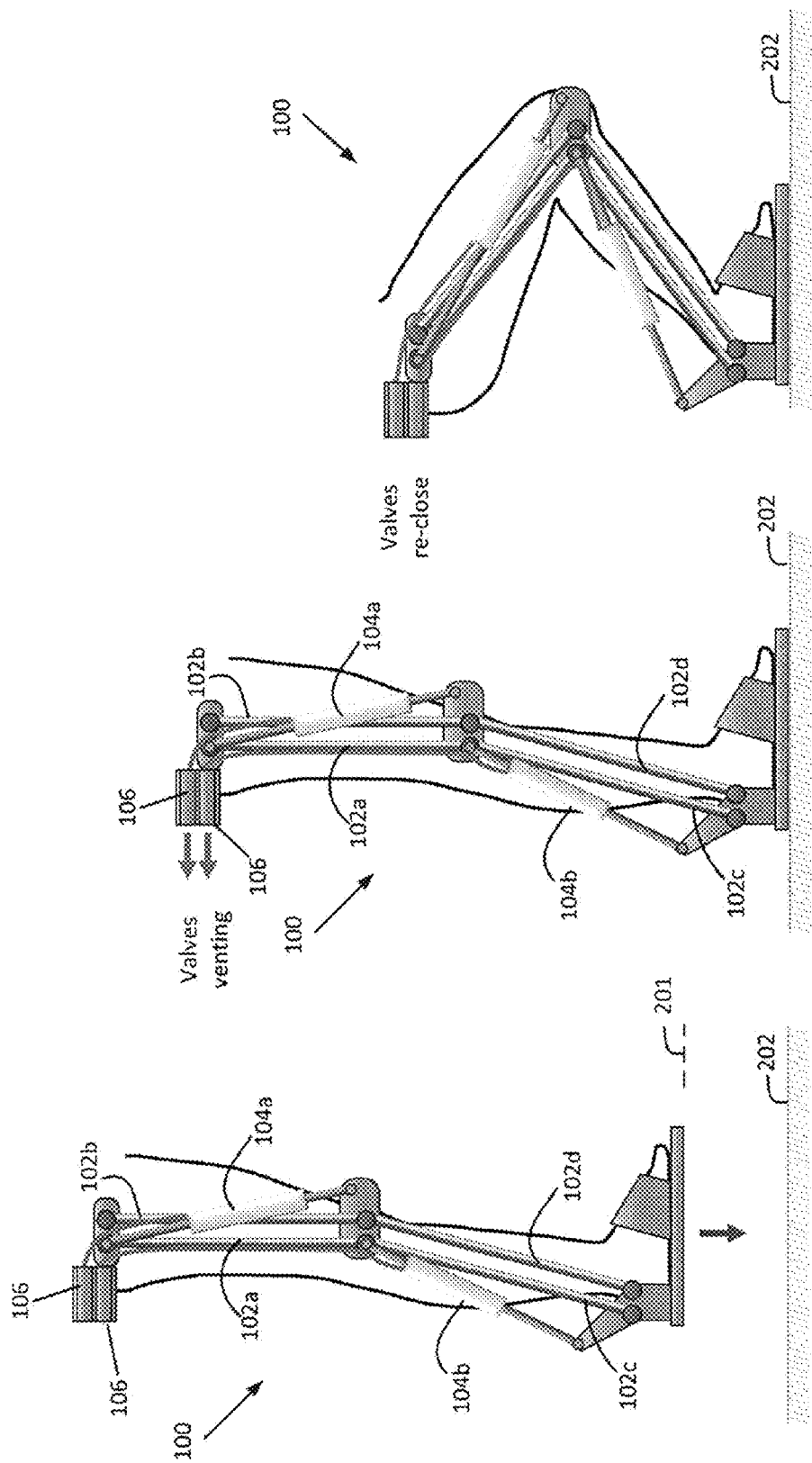
FIG. 2A is a first figure in a series that is useful for showing how the exoskeleton in FIG. 1 can be controlled to improve operator safety.
FIG. 2B is a second figure in a series that is useful for showing how the exoskeleton in FIG. 1 can be controlled to improve operator safety.
FIG. 2C is a third figure in a series that is useful for showing how the exoskeleton in FIG. 1 can be controlled to improve operator safety.

The safety performance of an exoskeleton under certain conditions can be improved with an automatic fall-activated safety behavior. In the event that an uncontrolled fall is detected, the control system 107 automatically re-configures one or more of the motion actuators to transition from a first state in which they perform conventional actuator operations, to a second state in which the same actuators exclusively function instead as energy dampers which dissipate the shock load from a fall. When the conditions associated with the uncontrolled fall are deemed to have passed, the actuators transition back to their first operating state. The inventive arrangements are illustrated in FIGS. 2A, 2B and 2C which show a series of actions associated with the lower body portion of an exoskeleton 100. It should be noted that certain components of the exoskeleton 100 are not shown in FIGS. 2A-2C so as to avoid obscuring the invention. Also, it should be noted that while such figures depict only a lower body portion of an exoskeleton, the inventive arrangements are applicable to any of the moving components of an exoskeleton, including upper body elements (from the waist up) and lower body elements (from the waist down).

The sensor 120 provided in an exoskeleton 100 as described herein can advantageously be used to facilitate detection of a condition where the exoskeleton as worn by a user is falling or otherwise experiencing uncontrolled downward movement from a higher level 201 to a lower level 202. Such falling condition will usually be indicated by uncontrolled acceleration in a downward direction (higher level to lower level relative to the surface of the earth) due to the forces of gravity. The initial occurrence of a falling condition is illustrated in FIG. 1A. In such a scenario, the control system automatically controls some (or all) of the valves 106 associated with the motion actuators 104a, 104b to cause the motion actuators to transition from a first state in which they are used to cause movement of the exoskeleton structure, to a second state in which they are used to dissipate the shock load from a fall.

If the motion actuators are pneumatic cylinders (or other type pneumatic actuator) the transition to the second operational state is effected by allowing a controlled venting of air from inside a cylinder of a pneumatic piston to allow the air internal of the piston to vent to the external environment. In this condition the pneumatic cylinder no longer provides a motive force which moves the structural element but instead serves exclusively as a shock absorber or energy damper. The venting of air in this way is shown in FIG. 1B. The valves 106 continue to allow air to vent (i.e., the motion actuator remains in the second operational state) as the structural elements 104a, 104b, 104c, 104d comprising the exoskeleton displace or rotate from the position in FIG. 1B to the position shown in FIG. 1C. As the structural elements displace in this way, the motion actuators 102a, 102b serve as dampers, absorbing the energy and shock associated with the fall.

The venting action will temporarily interrupt normal actuator functions and instead cause the motion actuators 104a, 104b to function exclusively as dampers or shock absorbers. Notably, in such a scenario, a pneumatic actuator as described herein is back-drivable and capable of dissipating energy. Similarly, a hydraulic actuator and electric motor actuator are each back-drivable in response to external forces applied to them. Consequently, if the actuator is reconfigured to function as an energy damper, impact energy associated with the exoskeleton striking the ground is advantageously absorbed by the damper rather than being communicated to a user who is wearing the exoskeleton 100. The valves 106 used to vent the motion actuators can be configured to have only two states (open and closed). Alternatively, an opening defined by a valve orifice can be selectively controlled to vary the size of an opening provided for venting air. By varying the size of the valve orifice a damping coefficient of the pneumatic actuator can be selectively modified. For example, an orifice of a valve 106 can be opened only a small amount to provide a larger damping coefficient (stiffer damper) as compared to a valve orifice that provides a larger opening for the escape of compressed air. A valve orifice with a relatively larger opening will have a relatively smaller magnitude damping coefficient.

Damping as described herein can be thought of as drag or a force that opposes movement of an object. To this end, damping is sometimes modelled as a force synchronous with the velocity of the object but opposite in direction to it. For example a simple mechanical viscous damper can provide a damping force that is proportional to the velocity of an object. In such a scenario, a damping force F experienced by an object can be calculated based on the velocity v of such object by using the equation $F=-cv$, where c is a damping coefficient that may be expressed in units of newton-seconds per meter.

In some scenarios, it can be advantageous to vary the magnitude of a drag coefficient c over time while the motion actuator is in the second operational state and functioning as a damper. For example, when a fall occurs as shown in FIG. 2C, the exoskeleton will at some point impact a surface at lower level 202. Assume that the occurrence of this initial impact is shown in FIG. 2B. Due to the downward acceleration of the exoskeleton which occurs in FIG. 2A, the control system 107 will cause the motion actuators to be in their second state. In this second state, energy damping will occur during a period of time as the exoskeleton transitions from the condition shown in FIG. 2B to the condition shown in FIG. 2C. In accordance with one aspect of the invention, one or more of the motion actuators 104a, 104b can have a constant damping coefficient c during the entire period of time associated with this transition from the position shown in FIG. 1B to the position shown in FIG. 1C. The damping function of the motion actuators will provide a more controlled deceleration of the exoskeleton.

According to one aspect of the invention, at the moment of initial impact shown in FIG. 1B, it may be desirable to have a damping coefficient that is initially minimal (minimal damping force). The damping coefficient can be gradually increased (damping force increases) as the exoskeleton transitions to the condition shown in FIG. 1C. In other words, the damping coefficient can be varied over time as the exoskeleton comes to a resting state shown in FIG. 1C. Once damping operations are complete, the one or more motion actuator 104a, 104b can be caused by controller 107 to revert to the first operational state in which they once again provide motive force for effecting motion to the exoskeleton 100. Notably, the variation in the damping coefficient c can be linear or non-linear in accordance with control signals provided by control system 107. The magnitude and/or variation of the damping coefficient are advantageously selected to minimize the potential for user injuries resulting from the fall. The control system is advantageously configured to return the one or more motion actuators to the first operational state following termination of the uncontrolled acceleration.

In certain scenarios, a designer may find it advantageous to independently control a damping coefficient of two or more of the of motion actuators in the second state when a fall condition is detected. For example, in a fall such at the one shown in FIGS. 2A-2C it may be advantageous to provide different amounts of energy damping for a motion actuator 104a as compared to motion actuator 104b. Alternatively, a different amount of damping may be deemed desirable for an upper body portion (not shown) of the exoskeleton 100 versus the lower body portion of the exoskeleton. Accordingly, in such scenarios, the control system 107 can selectively control the configuration of the motion actuators (e.g. using valves 106) to independently vary their respective damping rates. The control system 107 can optionally receive sensor inputs which indicate at least one of a displacement, a force, and an acceleration experienced by two or more of the structural members. Then, based on such sensor data, the control system can independently vary the damping coefficient of certain motion actuators based on those sensor inputs.

When the one or more sensors provided on the exoskeleton indicate that the exoskeleton is at rest (fall condition terminated) the control system advantageously returns the valves 106 to their normal or nominal state so that the motion actuators can again be used mainly for effecting movement of the exoskeleton (as opposed to energy damping). For example, in FIG. 2C the pneumatic actuators have already absorbed the shock from the fall and so the valves 106 can be closed.

Figure 3:
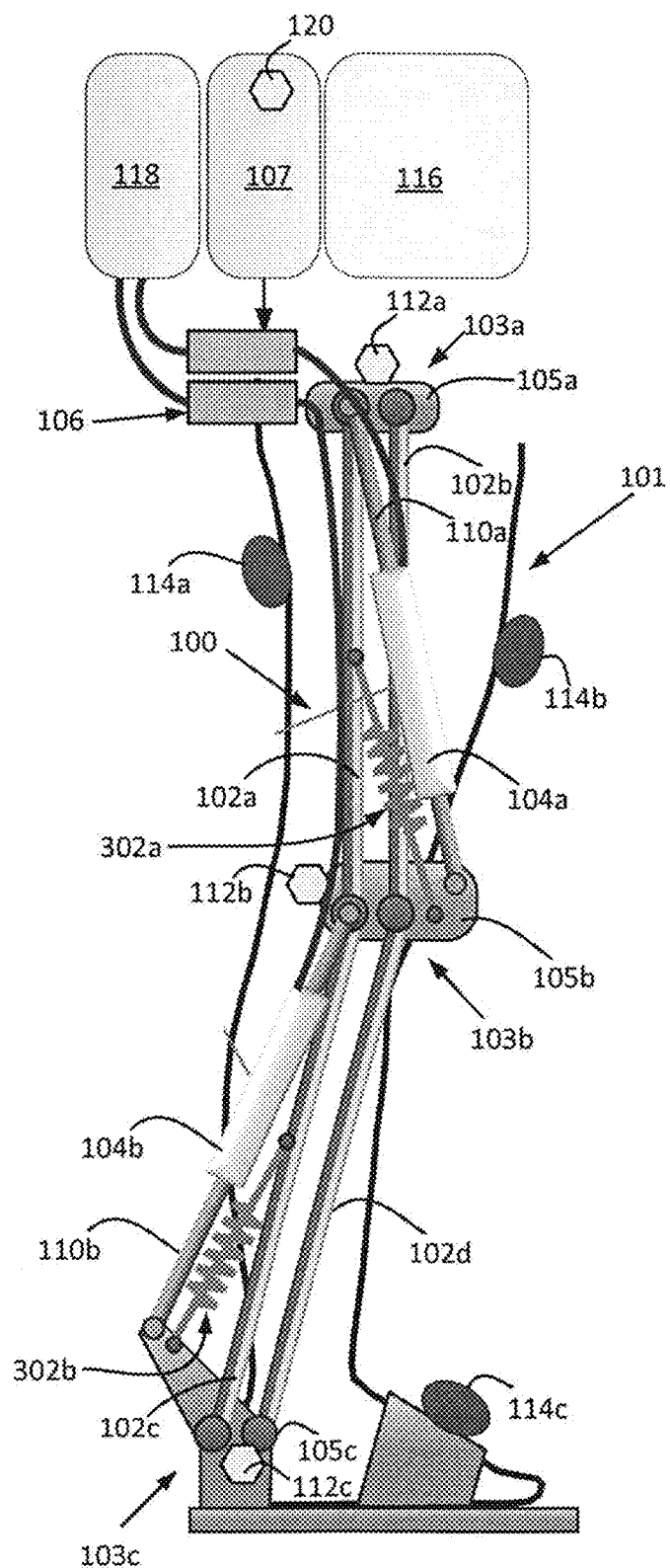
FIG. 3 shows an alternative embodiment of an exoskeleton in which static balancing springs are provided.

Further, it will be appreciated that performance of a system as described herein can in some scenarios be further improved by combining the automatic damping described above with a set of static balancing springs. Such an arrangement is shown in FIG. 3. The static balancing springs 302a, 302b will statically balance an exoskeleton system 100 so that the various movable structural elements 102a, 102b, 102c, 102d are in static equilibrium throughout its range of motion. Such an arrangement can reduce the power consumed by motion actuators 104a, 104b under certain circumstances. The most common example of a statically balanced system is a spring-supported desk lamp. A statically balanced mechanism has constant potential energy regardless of configuration. Accordingly, such as system does not require any actuator effort to support the mechanism's weight. In a system such at the one shown in FIG. 3, a damping coefficient can be selected by a designer to minimize system oscillations in the event of a fall, while damping impact energy to prevent user injury.

Figure 4:
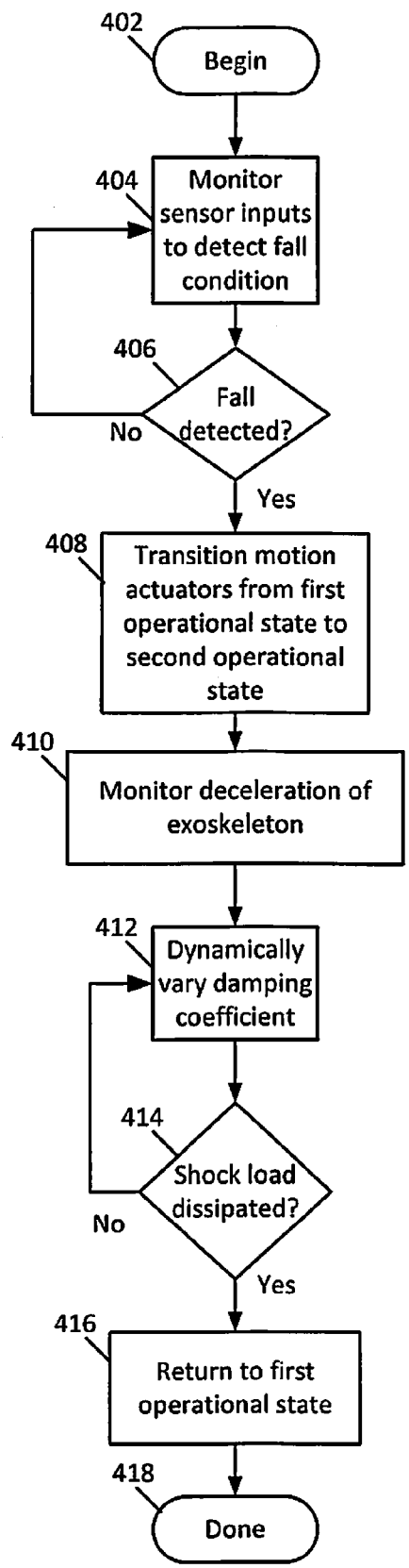
FIG. 4 is a flowchart that is useful for understanding a method of controlling an exoskeleton for improved operator safety.

Referring now to FIG. 4, a flowchart is provided that is useful for understanding the inventive arrangements. A method for preventing injury to a user of a robotic exoskeleton 100 can begin at 402 and continues at 404 wherein a control system 107 monitors one or more sensor inputs to determine the occurrence of an uncontrolled acceleration of at least a portion of the exoskeleton, as might occur during a fall. At 406, a determination is made as to whether a fall condition has been detected. If a fall no fall has been detected (406: No), the process returns to 404 and monitoring continues. However, if a fall condition is detected (406: Yes) then the process continues to 408 and the control system causes at least one motion actuator to automatically transition from the first operational state to the second operational state.

In the first operational state, the one or more motion actuators are configured to provide a motive force for controlled movement of the exoskeleton. In the second operational state, the one or more motion actuators are configured to function as energy dampers which dissipate a shock load exerted upon the exoskeleton. Thereafter, the control system at 410 continues to monitor one or more dynamic parameters of the exoskeleton to detect first an impact of the exoskeleton and then a subsequent deceleration. This will generally involve monitoring outputs from one or more of the sensors provided on the exoskeleton. The control system 107 is optionally configured to perform step 412 in which a damping coefficient of one or more motion actuators is dynamically varied during the time that the motion actuator is in the second operational state. Alternatively, the motion actuators can be configured to have a constant damping coefficient.

At 414, a determination is made as to whether the shock load from the fall (i.e. from the exoskeleton impacting at lower level 202) has been fully dissipated. For example, the control system can conclude that the shock load has been dissipated when one or more sensor inputs indicate that the exoskeleton is at rest and no longer is decelerating. Once this condition has occurred (414: Yes) the process can return to the first operational state at 416. Thereafter, the process can terminate at 418. Alternatively, the process can return to step 404 and continue.

Although the invention has been illustrated and described with respect to one or more implementations, equivalent alterations and modifications will occur to others skilled in the art upon the reading and understanding of this specification and the annexed drawings. In addition, while a particular feature of the invention may have been disclosed with respect to only one of several implementations, such feature may be combined with one or more other features of the other implementations as may be desired and advantageous for any given or particular application. Thus, the breadth and scope of the present invention should not be limited by any of the above described embodiments. Rather, the scope of the invention should be defined in accordance with the following claims and their equivalents.

We claim:

1. An exoskeleton system, comprising:
   an exoskeleton configured to be worn by a human operator;
   an exoskeleton control system;
   a plurality of motion actuators responsive to the exoskeleton control system to cause movement of a plurality of structural members comprising the exoskeleton;
   a plurality of sensors which sense movement of a plurality of human body parts associated with the human operator and communicate sensor data concerning such movement to the exoskeleton control system;
   the exoskeleton control system responsive to the sensor data for actuating the plurality of motion actuators to cause movement of the exoskeleton which corresponds to the movement of the plurality of human body parts which has been sensed;
   wherein the plurality of motion actuators is arranged to selectively transition in response to signals from the exoskeleton control system from a first operational state to a second operational state;
   wherein each motion actuator of said motion actuators in the first operational state is configured to provide a motive force for controlled movement of the exoskeleton's structure, and in the second operational state is configured to function as a damper to dissipate a shock load exerted upon the exoskeleton; and
   wherein the exoskeleton control system (a) causes the transition to the second operational state to be initiated in response to a detection of an occurrence of an uncontrolled acceleration of at least a portion of the exoskeleton, and (b) dynamically varies during a period of time a damping coefficient of at least one motion actuator of said plurality of motion actuators in a linear or non-linear manner when in the second operational state.

2. The exoskeleton system according to claim 1, wherein the exoskeleton is comprised of a structural framework formed of a plurality of rigid structural members connected to each other at a plurality of joint locations where a plurality of robot joints are provided, the joint locations and the robot joints arranged to facilitate movement of the rigid structural members in a manner that at least partially corresponds to movement in accordance with the human anatomy of a user when a suit is worn.

3. The exoskeleton system according to claim 2, wherein the plurality of rigid structural members and the plurality of robot joints are arranged so that the exoskeleton can be fitted to and move with at least one part of a user selected from the group consisting of an upper body portion which extends above the waist, a lower body portion which extends below the waist, and a full body portion comprising the upper and lower body.

4. The exoskeleton system according to claim 1, wherein the exoskeleton control system is responsive to at least one sensor input to detect an occurrence of an uncontrolled acceleration of at least a portion of the exoskeleton.

5. The exoskeleton system according to claim 4, wherein the exoskeleton control system is configured to return the motion actuators to the first operational state following termination of the uncontrolled acceleration.

6. The exoskeleton system according to claim 4, wherein the uncontrolled acceleration comprises a fall from a higher level toward a relatively lower level.

7. The exoskeleton system according to claim 4, wherein the control system gradually increases the damping coefficient of said motion actuator when in the second operational state.

8. An exoskeleton system, comprising:
   an exoskeleton configured to be worn by a human operator;
   an exoskeleton control system;
   a plurality of motion actuators responsive to the control system to cause movement of a plurality of structural members comprising the exoskeleton;
   a plurality of sensors which sense movement of a plurality of human body parts associated with the operator and communicate sensor data concerning such movements to the exoskeleton control system; and
   the control system responsive to the sensor data for actuating the plurality of motion actuators to cause movement of the exoskeleton which corresponds to the movement of the human body parts which has been sensed;
   wherein the motion actuators are arranged to selectively transition in response to signals from the control system signals from a first operational state to a second operational state;
   wherein said motion actuators in the first operational state are configured to provide a motive force for controlled movement of the exoskeleton structure, and in the second operational state are configured to function as a damper to dissipate a shock load exerted upon the exoskeleton;
   wherein the control system is responsive to at least one sensor input to detect an occurrence of an uncontrolled acceleration of at least a portion of the exoskeleton, and wherein said control system causes the transition to the second state to be initiated responsive to sensing the occurrence of the uncontrolled acceleration;

wherein the control system gradually increases a damping coefficient of at least one of said plurality of motion actuators when in the second operational state; and wherein the damping coefficient is linearly varied during a period of time while in the second operational state.

9. An exoskeleton system, comprising:

an exoskeleton configured to be worn by a human operator;

an exoskeleton control system;

a plurality of motion actuators responsive to the control system to cause movement of a plurality of structural members comprising the exoskeleton;

a plurality of sensors which sense movement of a plurality of human body parts associated with the operator and communicate sensor data concerning such movements to the exoskeleton control system; and the control system responsive to the sensor data for actuating the plurality of motion actuators to cause movement of the exoskeleton which corresponds to the movement of the human body parts which has been sensed;

wherein the motion actuators are arranged to selectively transition in response to signals from the control system signals from a first operational state to a second operational state;

wherein said motion actuators in the first operational state are configured to provide a motive force for controlled movement of the exoskeleton structure, and in the second operational state are configured to function as a damper to dissipate a shock load exerted upon the exoskeleton;

wherein the control system is responsive to at least one sensor input to detect an occurrence of an uncontrolled acceleration of at least a portion of the exoskeleton, and wherein said control system causes the transition to the second state to be initiated responsive to sensing the occurrence of the uncontrolled acceleration;

wherein the control system gradually increases a damping coefficient of at least one of said plurality of motion actuators when in the second operational state; and wherein the damping coefficient is varied in a non-linear manner during a period of time while in the second operational state.

10. An exoskeleton system, comprising:

an exoskeleton configured to be worn by a human operator;

an exoskeleton control system;

a plurality of motion actuators responsive to the control system to cause movement of a plurality of structural members comprising the exoskeleton;

a plurality of sensors which sense movement of a plurality of human body parts associated with the operator and communicate sensor data concerning such movements to the exoskeleton control system; and the control system responsive to the sensor data for actuating the plurality of motion actuators to cause movement of the exoskeleton which corresponds to the movement of the human body parts which has been sensed;

wherein the motion actuators are arranged to selectively transition in response to signals from the control system signals from a first operational state to a second operational state;

wherein said motion actuators in the first operational state are configured to provide a motive force for controlled movement of the exoskeleton structure, and in the second operational state are configured to function as a damper to dissipate a shock load exerted upon the exoskeleton;

wherein the control system is responsive to at least one sensor input to detect an occurrence of an uncontrolled acceleration of at least a portion of the exoskeleton, and wherein said control system causes the transition to the second state to be initiated responsive to sensing the occurrence of the uncontrolled acceleration; and wherein a damping coefficient of two or more of said plurality of motion actuators are independently varied by said control system when in the second operational state.

11. The exoskeleton system according to claim 10, wherein said control system receives sensor inputs which indicate at least one of a displacement, a force, and an acceleration experienced by two or more of the structural members, and independently varies said damping coefficient of said two or more motion actuators responsively to said sensor inputs when in the second operational state.

12. An exoskeleton system, comprising:

an exoskeleton configured to be worn by a human operator;

an exoskeleton control system;

a plurality of motion actuators responsive to the control system to cause movement of a plurality of structural members comprising the exoskeleton;

a plurality of sensors which sense movement of a plurality of human body parts associated with the operator and communicate sensor data concerning such movements to the exoskeleton control system; and the control system responsive to the sensor data for actuating the plurality of motion actuators to cause movement of the exoskeleton which corresponds to the movement of the human body parts which has been sensed;

wherein the motion actuators are arranged to selectively transition in response to signals from the control system signals from a first operational state to a second operational state;

wherein said motion actuators in the first operational state are configured to provide a motive force for controlled movement of the exoskeleton structure, and in the second operational state are configured to function as a damper to dissipate a shock load exerted upon the exoskeleton; and wherein at least one of the motion actuators is a pneumatic actuator and said control system is configured to facilitate controlled venting of air from within the pneumatic actuator in said second state, whereby the pneumatic actuator is caused to function as a damper.

13. The exoskeleton system according to claim 1, wherein at least one of the motion actuators is an electric motor and said control system electrically couples the electric motor to an electrical load in said second operational state to cause the electric motor to function as a damper.

14. An exoskeleton system, comprising:

an exoskeleton configured to be worn by a human operator;

an exoskeleton control system;

a plurality of motion actuators responsive to the control system to cause movement of a plurality of structural members comprising the exoskeleton;

a plurality of sensors which sense movement of a plurality of human body parts associated with the operator and communicate sensor data concerning such movements to the exoskeleton control system; and the control system responsive to the sensor data for actuating the plurality of motion actuators to cause movement of the exoskeleton which corresponds to the movement of the human body parts which has been sensed;

wherein the motion actuators are arranged to selectively transition in response to signals from the control system signals from a first operational state to a second operational state;

wherein said motion actuators in the first operational state are configured to provide a motive force for controlled movement of the exoskeleton structure, and in the second operational state are configured to function as a damper to dissipate a shock load exerted upon the exoskeleton; and wherein at least one of the motion actuators is a hydraulic actuator and the control system is configured to selectively route hydraulic fluid from said actuator to a baffle when in the second state to cause the hydraulic actuator to function as a damper.

15. A method for preventing injury to a user of an exoskeleton, comprising:
processing, by a control system, sensor data to detect an occurrence of an uncontrolled acceleration of at least a portion of the exoskeleton;
responsive to the detecting, performing operations by the control system to selectively control the exoskeleton to transition at least one motion actuator from (a) a first operational state in which the motion actuator is configured to provide a motive force for controlled movement of the exoskeleton to (b) a second operational state in which the at least one motion actuator is configured to function as a damper to dissipate a shock load exerted upon the exoskeleton; and
performing operations by the control system to dynamically vary during a period of time a damping coefficient of the at least one motion actuator in a linear or non-linear manner when in the second operational state.

16. The method according to claim 15, further comprising returning the at least one motion actuator to the first operational state after the shock load has been dissipated.

17. The method according to claim 15, wherein the damping coefficient of the at least one motion actuator is gradually increased during the second operational state.

18. The method according to claim 17, further comprising selectively controlling the gradual increase to provide a linear variation in the damping coefficient over time.

19. A method for preventing injury to a user of an exoskeleton, comprising:
detecting an occurrence of an uncontrolled acceleration of at least a portion of the exoskeleton;
responsive to the detecting, selectively controlling the exoskeleton to transition at least one motion actuator from a first operational state in which the motion actuator is configured to provide a motive force for controlled movement of the exoskeleton, to a second operational state in which the at least one motion actuator is configured to function as a damper to dissipate a shock load exerted upon the exoskeleton while in the second operational state, gradually increasing a damping coefficient of the at least one motion actuator; and
selectively controlling the gradual increase to provide a non-linear variation in the damping coefficient over time.

20. A method for preventing injury to a user of an exoskeleton, comprising:
detecting an occurrence of an uncontrolled acceleration of at least a portion of the exoskeleton;
responsive to the detecting, selectively controlling the exoskeleton to transition at least one motion actuator from a first operational state in which the motion actuator is configured to provide a motive force for controlled movement of the exoskeleton, to a second operational state in which the at least one motion actuator is configured to function as a damper to dissipate a shock load exerted upon the exoskeleton; and
transitioning two or more of the motion actuators to the second state to dissipate the shock load, and independently varying a damping coefficient of the two or more motion actuators when in the second operational state.

21. The method according to claim 20, further comprising analyzing one or more sensor inputs which indicate at least one of a displacement, a force, and an acceleration experienced by two or more structural members comprising the exoskeleton, and independently varying the damping coefficient of the two or more motion actuators responsive to the sensor inputs when in the second operational state.

* * * * *